US012725257B2

(12) United States Patent
Sim et al.

(10) Patent No.: US 12,725,257 B2
(45) Date of Patent: Sep. 1, 2026

(54) SURGICAL STAGE IMAGE TRANSMISSION METHOD AND SYSTEM USING SAME

(71) Applicant: MediThinQ Co., Ltd., Seongnam-si (KR)

(72) Inventors: Ji Woo Sim, Yongin-si (KR); Na Young Kim, Yeoju-si (KR); Yoon Sang Jung, Seongnam-si (KR)

(73) Assignee: MEDITHINQ CO., LTD., Seongnam-si (KR)

( * ) Notice: Subject to any disclaimer, the term of this patent is extended or adjusted under 35 U.S.C. 154(b) by 0 days.

(21) Appl. No.: 19/122,624

(22) PCT Filed: Sep. 19, 2023

(86) PCT No.: PCT/KR2023/014133

§ 371 (c)(1),
(2) Date: Apr. 18, 2025

(87) PCT Pub. No.: WO2024/085467

PCT Pub. Date: Apr. 25, 2024

(65) Prior Publication Data

US 2026/0011008 A1 Jan. 8, 2026

(30) Foreign Application Priority Data

Oct. 20, 2022 (KR) ........................ 10-2022-0135530

(51) Int. Cl.
*G06T 7/00* (2017.01)
*G16H 10/60* (2018.01)
(Continued)

(52) U.S. Cl.
CPC ........... *G06T 7/0012* (2013.01); *G16H 10/60* (2018.01); *G16H 20/40* (2018.01); *G16H 30/20* (2018.01);
(Continued)

(58) Field of Classification Search
None
See application file for complete search history.

(56) References Cited

U.S. PATENT DOCUMENTS 5,924,074 A * 7/1999 Evans .................... G16H 20/10 707/999.001
2020/0273557 A1* 8/2020 Wolf ...................... G06V 20/41
2021/0173888 A1* 6/2021 Flack .................. G06F 16/9017

FOREIGN PATENT DOCUMENTS

KR 10-2010-0058786 A 6/2010
KR 10-2019-0080706 A 7/2019
(Continued)

OTHER PUBLICATIONS

Office Action dated Jan. 11, 2023 for Korean Application No. 10-2022-0135530 with English translation.

*Primary Examiner* — Devin C Hein
(74) *Attorney, Agent, or Firm* — Birch, Stewart, Kolasch & Birch, LLP

(57) ABSTRACT

According to the present invention, a surgical stage image transmission system may be provided, the system comprising: a content server configured to store a plurality of surgery images; an image patch management server configured to receive surgery-related information including surgery type, and segment and store, on the basis of the surgery-related information, the plurality of surgery images stored in the content server, the surgery images being segmented on the basis of detailed surgical stages; a surgical stage determination server configured to determine detailed surgical stages on the basis of the type of surgery to be received by a patient and determine each image patch related to each of the detailed surgical stages; and a user terminal configured to receive a plurality of image patches on the basis of the detailed surgical stages determined in the surgical stage determination server.

6 Claims, 12 Drawing Sheets

(51) Int. Cl.

| | |
|---|---|
| ***G16H 20/40*** | (2018.01) |
| ***G16H 30/20*** | (2018.01) |
| ***G16H 40/20*** | (2018.01) |
| ***G16H 50/70*** | (2018.01) |

(52) U.S. Cl.
CPC ............. *G16H 40/20* (2018.01); *G16H 50/70* (2018.01); *G06T 2207/10016* (2013.01)

(56) References Cited

FOREIGN PATENT DOCUMENTS

| | | | |
|---|---|---|---|
| KR | 10-2020-0081161 | A | 7/2020 |
| KR | 10-2021-0089983 | A | 7/2021 |
| KR | 10-2021-0104190 | A | 8/2021 |
| KR | 10-2539691 | B1 | 6/2023 |

* cited by examiner

[FIG. 1]
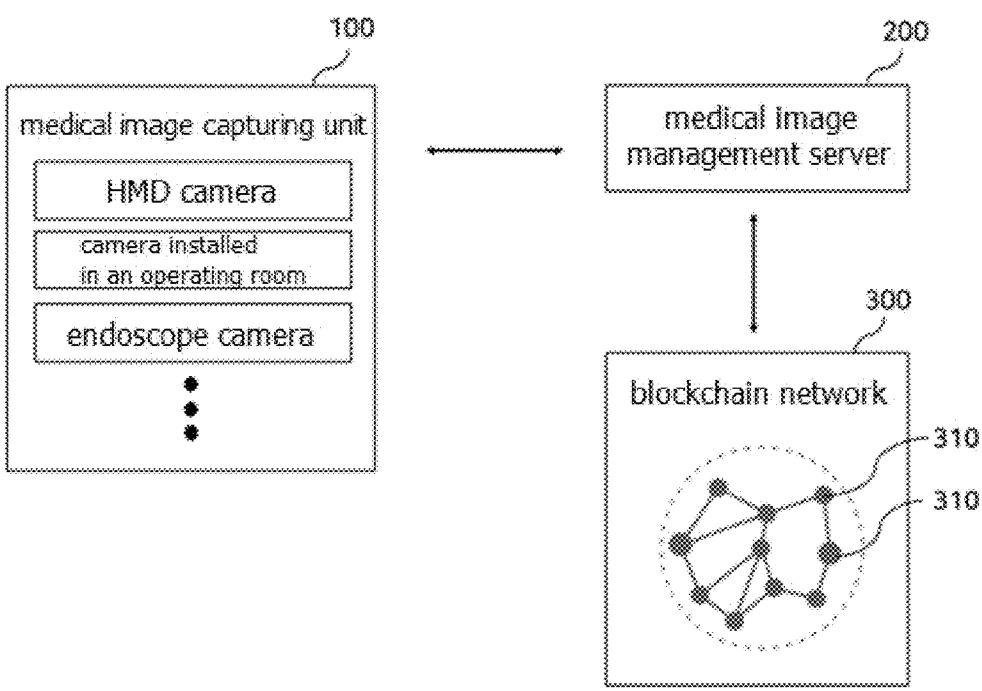

[FIG. 2]
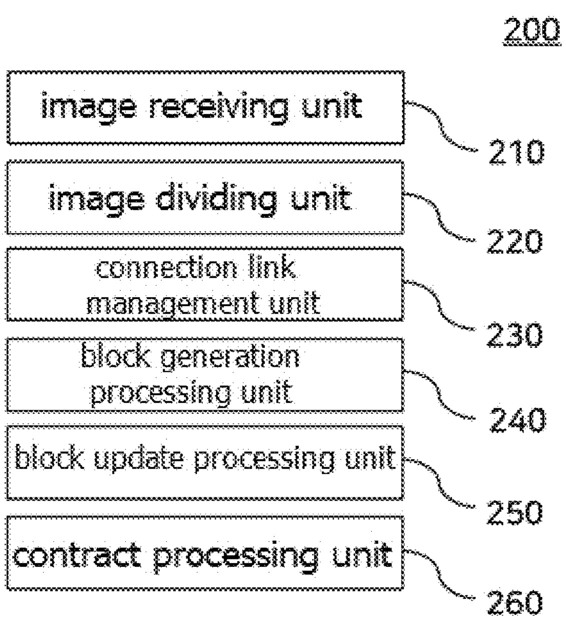

[FIG. 3]
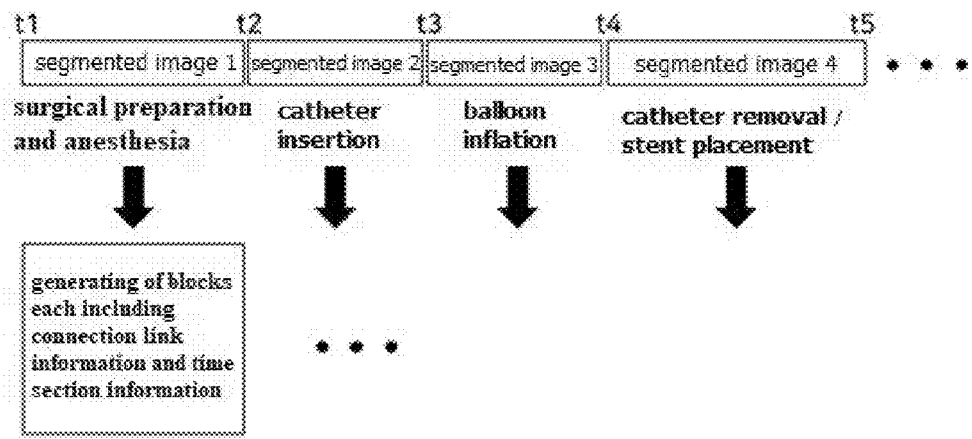

[FIG. 4]
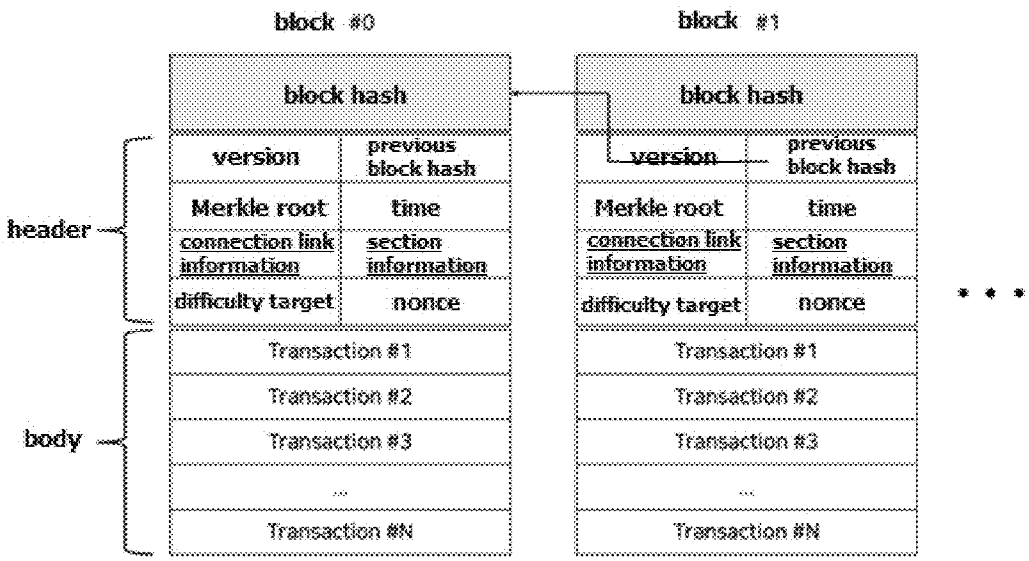

[FIG. 5]
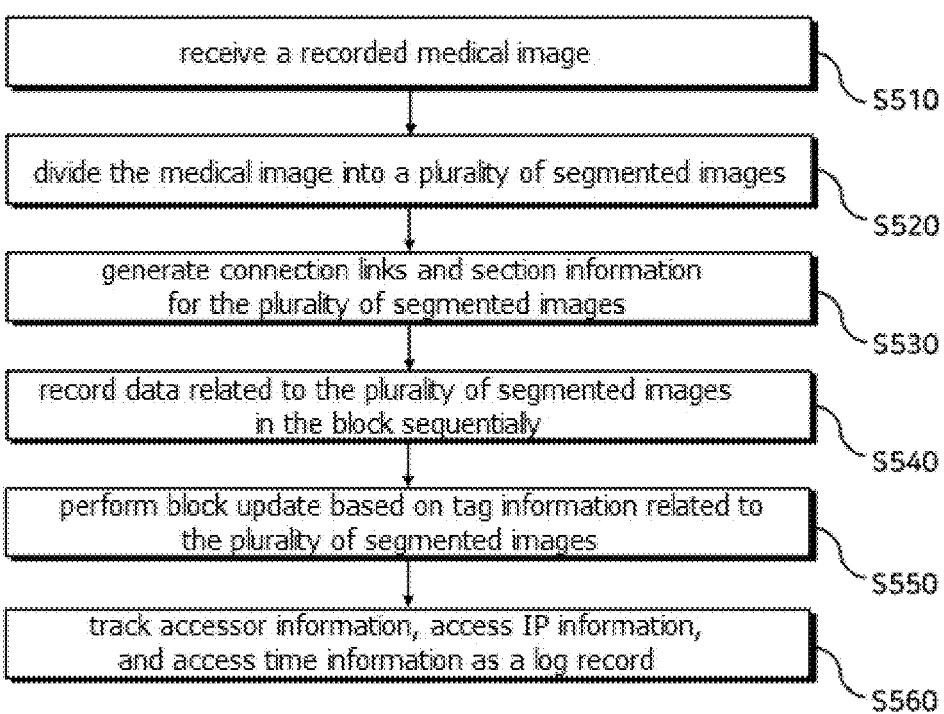

[FIG. 6]
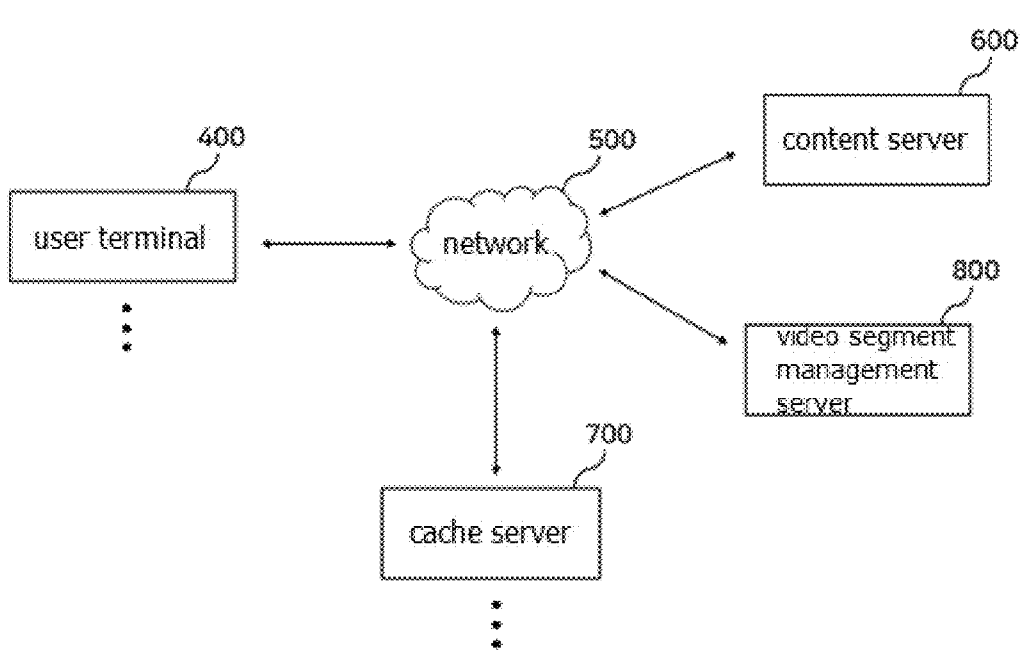

[FIG. 7]
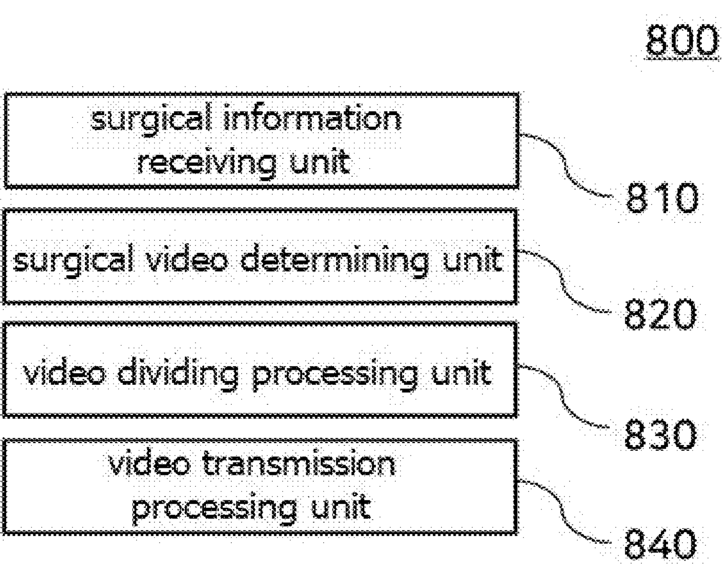

[FIG. 8]
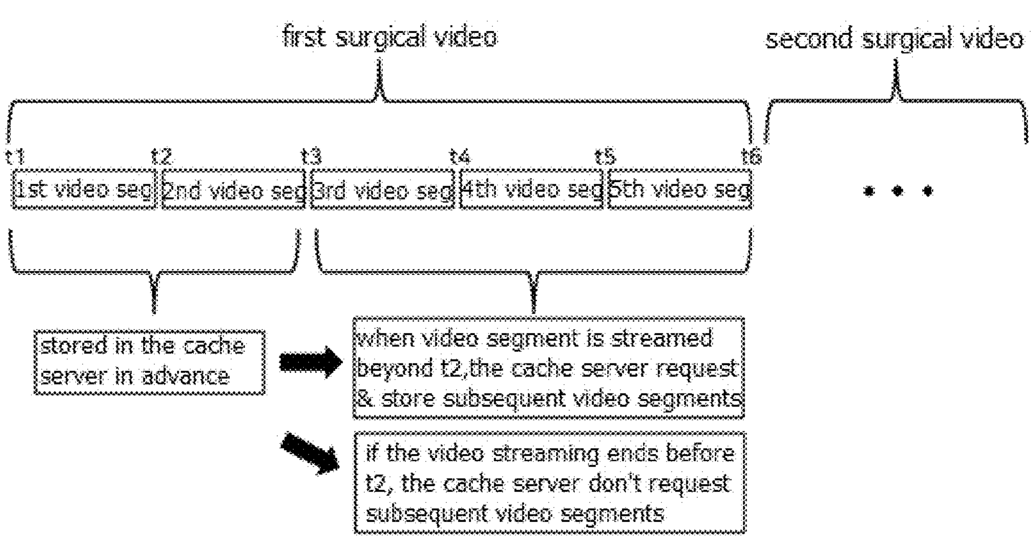

[FIG. 9]
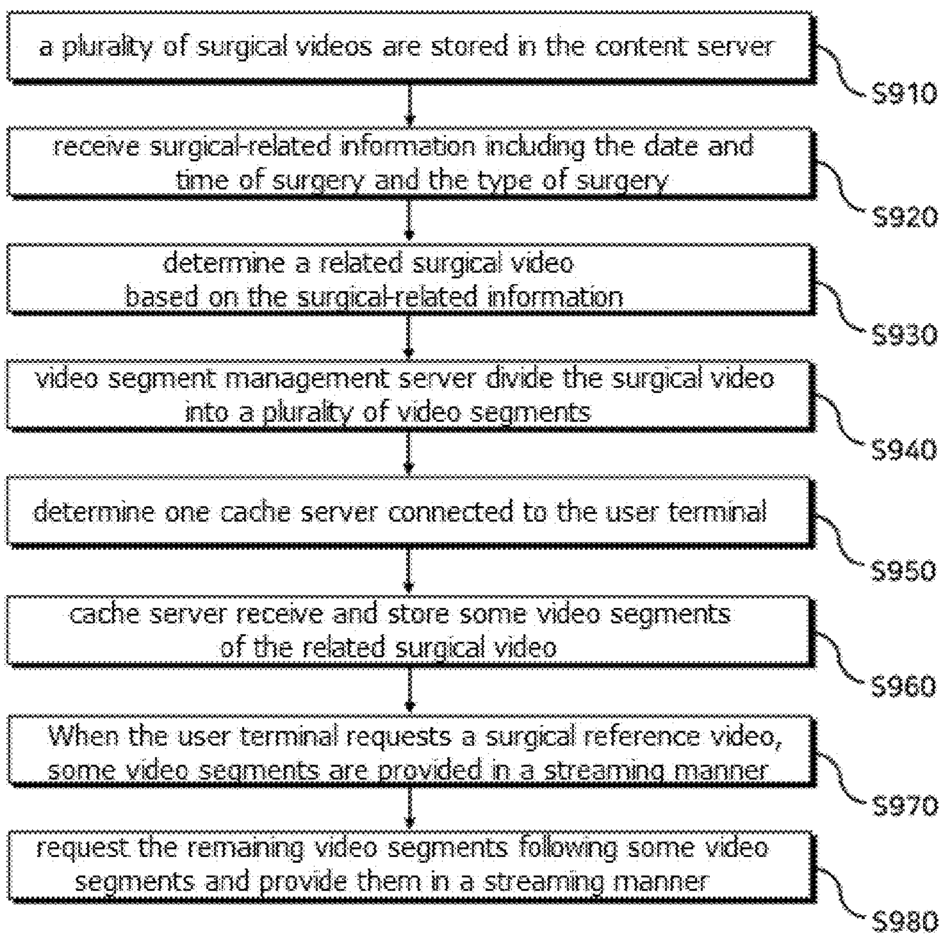

[FIG. 10]
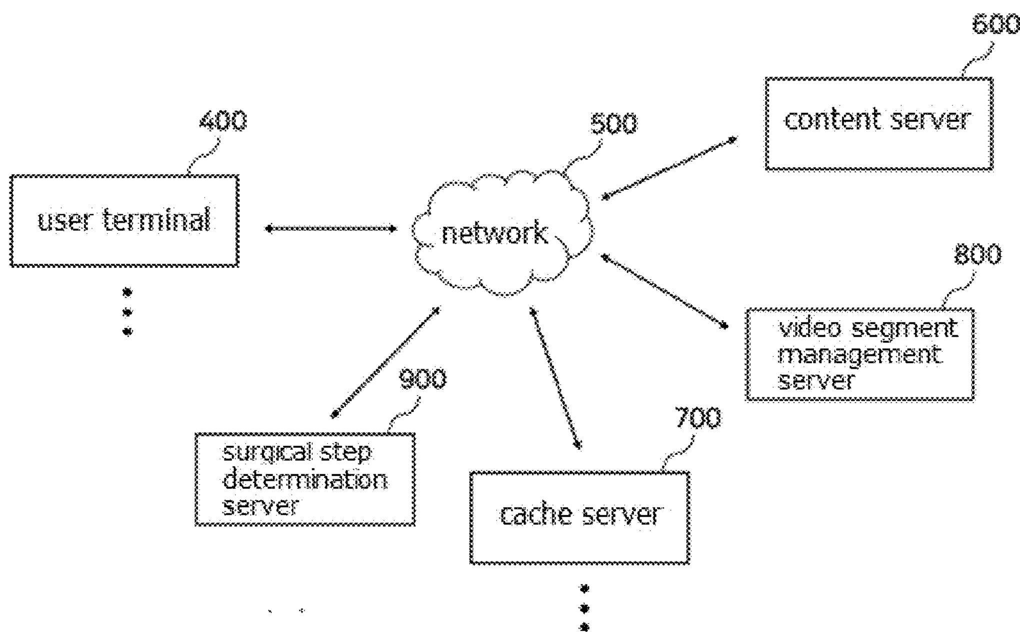

[FIG. 11]
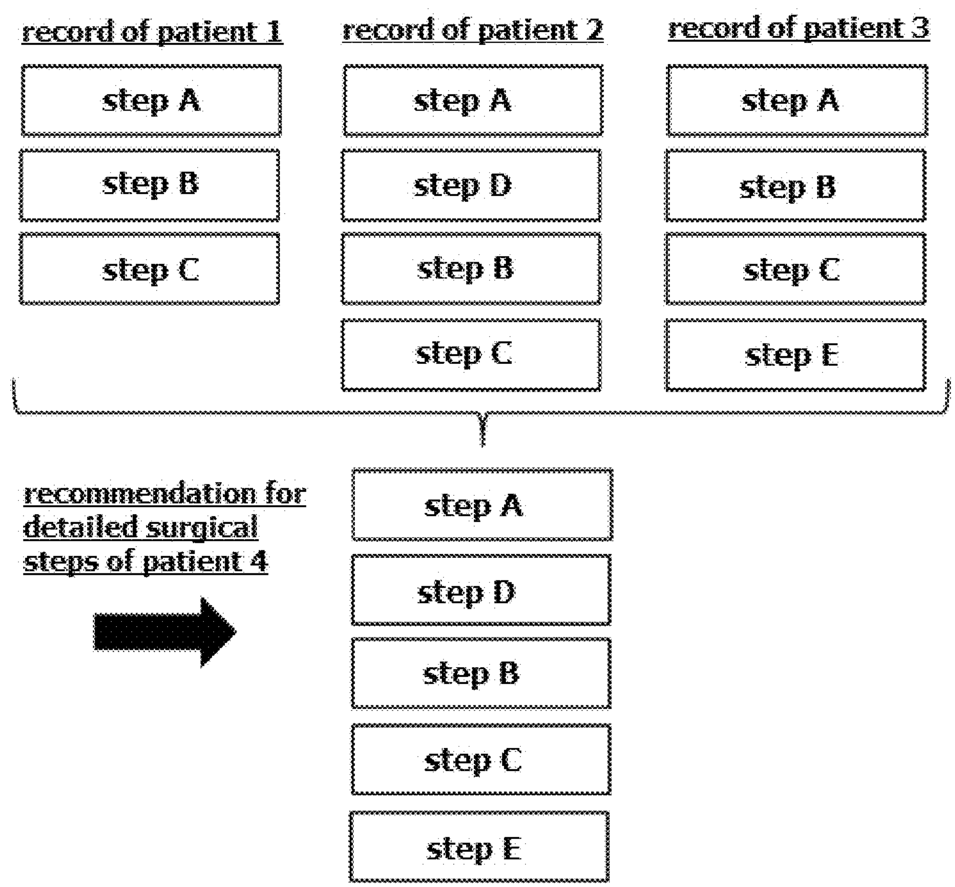

[FIG. 12]
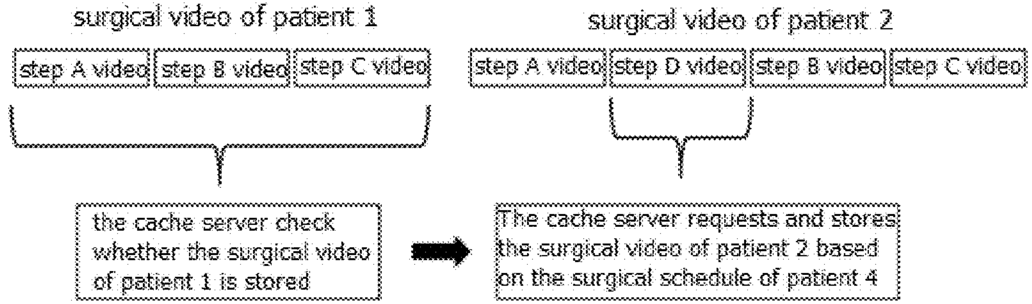

SURGICAL STAGE IMAGE TRANSMISSION METHOD AND SYSTEM USING SAME

CROSS REFERENCE TO RELATED APPLICATIONS

This application is the National Phase of PCT International Application No. PCT/KR2023/014133, filed on Sep. 19, 2023, which claims priority under 35 U.S.C. 119 (a) to Patent Application No. 10-2022-0135530, filed in the Republic of Korea on Oct. 20, 2022, all of which are hereby expressly incorporated by reference into the present application.

TECHNICAL FIELD

The present invention relates to a method and system for transmitting surgical step videos. More specifically, it relates to a method and system capable of generating and providing surgical videos related to optimal detailed surgical steps based on surgery-related information.

BACKGROUND ART

As multimedia technology has rapidly advanced and been applied in various fields recently, technology is being developed in the medical field to produce recorded videos of patient surgical scenes for doctors to present at medical conferences or utilize for other purposes.

Furthermore, surgical videos are often filmed for surgical records and as a defense against potential medical disputes. In cases of joint surgery, endoscopic surgery is frequently performed to diagnose and treat while visually checking lesions through a micro-camera. Recently, most medical equipment is equipped with video recording functions, leading to a rapid increase in surgical video filming.

These recorded surgical videos hold significant value for other doctors, patients, researchers, etc. In particular, if various medical information is added to the surgical videos, their utility and asset value can increase.

Accordingly, there is a need for a new method and system that can prevent tampering with medical video records and safely store and mediate their transactions. There is also a need for a method and system that can provide medical videos more quickly and stably without interruption during surgery. Furthermore, there is a need for a method and system that can more effectively provide detailed surgical step videos that surgeons or medical staff can refer to during surgery.

DETAILED DESCRIPTION OF THE INVENTION

Technical Problem

An object of the present invention is to provide a method and system capable of preventing tampering with surgical videos and preventing manipulation or disposal of surgical procedure records by, for example, separating a recorded video of a surgical scene into a plurality of video segments and managing the connection link information and interval information of each segment using a blockchain.

Another object of the present invention is to establish a system that can efficiently manage surgical recorded videos while reducing block data capacity by splitting the surgical recorded video into a plurality of video segments and constructing blocks using a combination of connection link information and interval information thereof.

Another object of the present invention is to establish a medical video management system that enables transparent management of the use and transaction of recorded surgical videos through transactions via smart contracts, thereby enabling monetization.

Another object of the present invention is to provide a method and system that can reduce buffering during playback of reference videos for surgeons or medical staff performing surgery and transmit surgical videos more quickly and stably using a cache server.

Another object of the present invention is to provide a cache server system capable of stably streaming a plurality of video segments, into which a surgical video is divided, to a user terminal without delay.

Another object of the present invention is to provide a video transmission system capable of generating and recommending optimal surgical videos based on information related to the ongoing surgery.

Another object of the present invention is to provide a surgical step video transmission system configured to determine more efficient and safer detailed surgical steps based on past surgical record information and transmit a plurality of video segments generated based thereon.

Another object of the present invention is to provide a method and system capable of recommending optimal detailed surgical steps suitable for a surgical patient using artificial intelligence technology and sequentially providing the detailed surgical step videos based thereon to the medical staff.

The technical problems to be solved by the present invention are not limited to those mentioned above, and other unmentioned technical problems will be clearly understood by those skilled in the art from the following description.

Solution for Problem

According to an embodiment of the present invention, there is provided a surgical step video transmission system comprising: a content server configured to store a plurality of surgical videos; a video segment management server configured to receive surgery-related information including a surgery type, and based on the surgery-related information, divide and store the plurality of surgical videos stored in the content server based on detailed surgical steps; a surgical step determination server configured to determine detailed surgical steps based on the surgery type of a surgical patient and determine respective video segments related to each detailed surgical step; and a user terminal configured to receive a plurality of video segments based on the detailed surgical steps determined by the surgical step determination server.

Furthermore, the surgical step determination server may be configured to determine the detailed surgical steps based on record information of a plurality of previous surgical patients who underwent the same type of surgery as the surgical patient.

Furthermore, the record information of the previous surgical patients may include at least one of gender, age, surgery timing, underlying diseases, history of other surgeries, post-operative prognosis, and surgical recovery period.

Furthermore, the surgical step determination server may be configured to determine the detailed surgical steps for the surgical patient by combining the detailed surgical steps of a first previous surgical patient who underwent the same type of surgery as the surgical patient and the detailed surgical steps of a second previous surgical patient who underwent the same type of surgery as the surgical patient.

Furthermore, the surgical step determination server may be configured to recommend the detailed surgical steps for the surgical patient through a learning model using artificial intelligence.

Furthermore, the system may further comprise a cache server configured to receive and store respective video segments related to each detailed surgical step from the video segment management server, and upon receiving a request for a detailed surgical step video from the user terminal, transmit the plurality of video segments related to the detailed surgical steps to the user terminal, wherein the cache server may be determined from a plurality of cache servers based on proximity to the user terminal's location or response speed.

Furthermore, the cache server may be configured to check whether the respective video segments related to each detailed surgical step determined by the surgical step determination server are stored, and for video segments not stored in the cache server, receive and store the corresponding video segments from the video segment management server based on the surgical schedule of the surgical patient.

According to another embodiment of the present invention, there is provided a surgical step video transmission method comprising: storing a plurality of surgical videos in a content server; receiving, at a video segment management server, surgery-related information including a surgery type, and based on the surgery-related information, dividing and storing the plurality of surgical videos stored in the content server based on detailed surgical steps; determining, at a surgical step determination server, detailed surgical steps based on the surgery type of a surgical patient and determining respective video segments related to each detailed surgical step; and receiving, at a user terminal, a plurality of video segments based on the detailed surgical steps determined by the surgical step determination server.

Effects of the Invention

According to the present invention, it is possible to provide a method and system capable of preventing tampering with surgical videos and preventing manipulation or disposal of surgical procedure records by, for example, separating a recorded video of a surgical scene into a plurality of video segments and managing the connection link information and interval information of each segment using a blockchain.

Furthermore, according to the present invention, it is possible to establish a system that can efficiently manage surgical recorded videos while reducing block data capacity by splitting the surgical recorded video into a plurality of video segments and constructing blocks using a combination of connection link information and interval information thereof.

Furthermore, according to the present invention, it is possible to establish a medical video management system that enables transparent management of the use and transaction of recorded surgical videos through transactions via smart contracts, thereby enabling monetization.

Furthermore, according to the present invention, it is possible to provide a method and system that can reduce buffering during playback of reference videos for surgeons or medical staff performing surgery and transmit surgical videos more quickly and stably using a cache server.

Furthermore, according to the present invention, it is possible to provide a cache server system capable of stably streaming a plurality of video segments, into which a surgical video is divided, to a user terminal without delay.

Furthermore, according to the present invention, it is possible to provide a video transmission system capable of generating and recommending optimal surgical videos based on information related to the ongoing surgery.

Furthermore, according to the present invention, it is possible to provide a surgical step video transmission system configured to determine more efficient and safer detailed surgical steps based on past surgical record information and transmit a plurality of video segments generated based thereon.

Furthermore, according to the present invention, it is possible to provide a method and system capable of recommending optimal detailed surgical steps suitable for a surgical patient using artificial intelligence technology and sequentially providing the detailed surgical step videos based thereon to the medical staff.

The effects of the present invention are not limited to those mentioned above, and other unmentioned effects will be clearly understood by those skilled in the art from the following description.

BRIEF DESCRIPTION OF DRAWINGS

FIG. 1 is a conceptual diagram illustrating the configuration of a system for managing medical video records using a blockchain according to an embodiment of the present invention.

FIG. 2 is a block diagram illustrating the configuration of a medical video management server according to an embodiment of the present invention.

FIG. 3 is an exemplary diagram illustrating the creation of blocks on a blockchain network for a plurality of video segments related to a medical video according to an embodiment of the present invention.

FIG. 4 is an exemplary diagram illustrating the header structure of a block according to an embodiment of the present invention.

FIG. 5 is a flowchart illustrating a method for managing medical videos using a blockchain according to an embodiment of the present invention.

FIG. 6 is a conceptual diagram illustrating the configuration of a surgical video transmission system using a cache server according to an embodiment of the present invention.

FIG. 7 is a block diagram illustrating the configuration of a video segment management server according to an embodiment of the present invention. (Note: The original text refers to a cache server here, but the description corresponds to the Video Segment Management Server 800 in FIGS. 6 & 7. Assuming a typo in the original and translating based on context and FIG. 7's likely content).

FIG. 8 is an exemplary diagram illustrating a method for providing a plurality of video segments related to a surgical video using a cache server according to an embodiment of the present invention.

FIG. 9 is a flowchart illustrating a surgical video transmission method using a cache server according to an embodiment of the present invention.

FIG. 10 is a conceptual diagram illustrating the configuration of a surgical step video transmission system using a cache server according to an embodiment of the present invention.

FIG. 11 is an exemplary diagram illustrating a configuration for recommending detailed surgical steps for a surgical patient according to an embodiment of the present invention.

FIG. 12 is an exemplary diagram illustrating a method for providing videos of detailed surgical steps using a cache server according to an embodiment of the present invention.

DETAILED DESCRIPTION FOR IMPLEMENTING THE INVENTION

Hereinafter, embodiments of the present invention will be described in detail with reference to the accompanying drawings so that those skilled in the art can easily carry out the invention. However, the present invention may be embodied in many different forms and is not limited to the embodiments described herein.

The terminology used herein is for the purpose of describing particular embodiments only and is not intended to be limiting of the invention. As used herein, the singular forms are intended to include the plural forms as well, unless the context clearly indicates otherwise.

As used herein, the terms "comprises" and/or "comprising" specify the presence of stated features, integers, steps, operations, elements, and/or components, but do not preclude the presence or addition of one or more other features, integers, steps, operations, elements, components, and/or groups thereof.

Furthermore, terms including ordinal numbers, such as "first," "second," etc., may be used to describe various components, but the components should not be limited by these terms. These terms are only used to distinguish one component from another. In addition, when describing the present invention, detailed descriptions of related known technologies that may obscure the gist of the present invention will be omitted.

Furthermore, the components illustrated in the embodiments of the present invention are shown independently to represent different characteristic functions, which does not mean that each component is constituted by a separate hardware or a single software configuration unit. That is, each component is listed as a respective component for convenience of description, and at least two components may be combined into one component, or one component may be divided into a plurality of components to perform functions. Embodiments in which components are integrated and embodiments in which components are separated are also included in the scope of the present invention as long as they do not depart from the essence of the present invention.

Hereinafter, embodiments according to the present invention will be described in detail with reference to the accompanying drawings. The configuration of the present invention and its operational effects will be clearly understood through the following detailed description.

FIG. 1 is a conceptual diagram illustrating the configuration of a system for managing medical video records using a blockchain according to an embodiment of the present invention.

The medical video management system may comprise a medical video capturing unit (100), a medical video management server (200), and a blockchain network (300). The medical video capturing unit (100) may be configured to record videos related to surgery, treatment, consultation, etc., in spaces such as operating rooms, treatment rooms, or consultation rooms within a hospital, and transmit the recorded medical videos to the medical video management server (200). The medical video capturing unit (100) may take various forms, such as a head-mounted display (HMD) camera wearable by medical staff like doctors, a camera installed in the operating room, an endoscopic camera used for endoscopic surgery, or multiple cameras or CCTVs. For example, a camera installed in the operating room ceiling can identify the initial position by specifying coordinates for each object in the initial real-time video and track movement by identifying the surgical scene and the surgeon's actions. Additionally, it can be configured to automatically capture and record the surgical scene by tracking the movement of all objects, such as surgical instruments being filmed, using image recognition technology.

The medical video management server (200) may be configured to receive medical videos recorded related to surgery or treatment using the medical video capturing unit (100), generate blocks on the blockchain network (300) based on data related to the medical videos, and update the blocks based on new data related to the medical videos. The medical video management server (200) may include memory for storing data and commands to manage information related to each module configured for receiving and managing medical videos, and a processor for executing the commands. A more specific configuration of the medical video management server (200) will be described with reference to FIG. 2.

The medical video management server (200) may be a server corresponding to one of the nodes constituting the blockchain network (300) or a server for managing the blockchain network (300). Blockchain technology is based on a Peer-to-Peer (P2P) method, where small data units are linked in a chain form to create blocks, storing management target data in this distributed data storage environment, making it impossible for anyone to arbitrarily modify it and allowing anyone to view the results of changes. Each block records all transaction details or state information propagated to users before the block was discovered. Since this is transmitted identically to all users via P2P, transaction details or state information cannot be arbitrarily modified or omitted. In the present invention, data or data bundles stored and updated via the blockchain network (300) for managing medical videos are referred to as 'blocks'.

FIG. 2 is a block diagram illustrating the configuration of a medical video management server according to an embodiment of the present invention.

The medical video management server (200) may include a video receiving unit (210), a video segmentation unit (220), a link management unit (230), a block generation processing unit (240), a block update processing unit (250), and a contract processing unit (260), etc. These components may include programs or program modules executable by one or more processors. The programs or program modules included in the medical video management server (200) may be configured in the form of an operating system, application program, or program, etc., and can be physically stored on various widely used types of storage devices. Such programs or program modules may include various forms such as one or more routines, subroutines, programs, objects, components, instructions, data structures, and for performing specific tasks or executing specific data types, but are not limited thereto.

First, the video receiving unit (210) is configured to receive medical videos recorded related to surgery or treatment using the medical video capturing unit (100), and can be connected to the medical video capturing unit (100) via wired or wireless internet.

The video segmentation unit (220) is configured to divide the medical video into a plurality of video segments. Based on the data related to these divided video segments, the block generation processing unit (240) can generate blocks corresponding to each segment information and record them sequentially. For example, the video segmentation unit (220) can sequentially generate a plurality of video segments from one medical video based on timestamp information set for each interval within the medical video. For instance, the timestamp information can be set for each stage by distinguishing detailed procedures within the surgery by the operating surgeon or medical staff, or it can be set automatically using artificial intelligence technology, etc. Furthermore, the plurality of video segments may further include tag information inserted into the recorded surgical video, and the tag information may include at least one of the surgical entity, comments related to the surgical situation, surgical sequence, surgical instruments, and surgery-related events. Such tag information can be associated with each timestamp information and entered by medical staff or automatically entered using artificial intelligence technology, etc.

The block generation processing unit (240) may be configured to generate blocks on the blockchain network (300) based on data related to the medical video. For example, it may be configured to generate a new block for each of the plurality of video segments. Furthermore, the header of the generated block may include information related to connection links accessible to each of the plurality of video segments. Also, the header of the generated block may further include interval information generated based on the timestamp information of the start and end times of each of the plurality of video segments.

The block update processing unit (250) may be configured to update block information based on tag information, etc., for the generated blocks. For example, it may include additional tag information corresponding to each video segment, viewing history, transaction history, usage history, etc. For example, it can track access information such as accessor information, access IP information, and access time for accesses made through the connection link of the corresponding video segment as log records, and update the body of the block corresponding to that video segment by recording this access information.

The contract processing unit (260) is configured to conclude various transaction contracts for the use of medical videos and process related processes. Such transaction contracts can be configured such that costs are settled according to pre-set transaction conditions using smart contracts. The contract processing unit (260) may be configured to generate blocks for smart contracts on the blockchain network (300) based on data related to the use of medical videos through smart contracts, and may include information such as the usage period information of the medical video, i.e., start and end dates, and information related to access and editing permissions for the corresponding video.

FIG. 3 is an exemplary diagram illustrating the creation of blocks on a blockchain network for a plurality of video segments related to a medical video according to an embodiment of the present invention.

Referring to FIG. 3, for example, a medical video related to a stent procedure or surgery can be divided into 4 video segments according to each stage: 1) Surgery preparation and anesthesia, 2) Catheter insertion, 3) Balloon inflation, 4) Catheter removal and stent placement. Each video segment can include interval information related to the start and end times as timestamp information, such as t1_t_2, t2_t_3, t3_t_4, t4_t_5. A different accessible connection link can be assigned to each divided video segment, and connection link information, which is information related to the connection link corresponding to each video segment, can be generated. Thus, a plurality of blocks can be generated for each of the plurality of video segments into which the medical video is sequentially divided, each block including connection link information and time interval information.

FIG. 4 is an exemplary diagram illustrating the header structure of a block according to an embodiment of the present invention.

The structure of a block can largely consist of a block hash acting as the block identifier, a header containing basic information, and a body containing transaction information, etc. Here, the header generally includes information such as version, previous block hash, Merkle root, time, difficulty target, and nonce. According to the present invention, the block header may further include connection link information related to connection links accessible to each of the plurality of video segments and interval information generated based on the timestamp information of the start and end times of each of the plurality of video segments.

Through such a block structure, by matching link information accessible to surgical video segments or still cuts for each fragmented and distributed ledger and recording it using blockchain, tampering with medical video records can be prevented. For example, by encrypting the link information and setting the storage space where the corresponding video or still cut is stored to read-only, modification of the corresponding video at the access location can be prevented.

The present invention can provide a system that efficiently manages surgical recorded videos while reducing block data capacity by splitting the surgical recorded video into a plurality of video segments and constructing blocks using a combination of connection link information and interval information. This can solve problems where surgical history is discarded due to expiration of the storage period or where key content related to the relevant surgery is tampered with.

FIG. 5 is a flowchart illustrating a method for managing medical videos using a blockchain according to an embodiment of the present invention.

Referring to FIG. 5, first, a medical video captured and recorded via the medical video capturing unit (100) can be received by the video receiving unit (210) of the medical video management server (200) (S510).

The medical video management server (200) can sequentially divide the medical video into a plurality of video segments via the video segmentation unit (220) (S520).

The medical video management server (200) can generate connection links for the plurality of video segments and generate interval information for each video segment via the link management unit (230) (S530).

The medical video management server (200) can sequentially record data related to the plurality of video segments into blocks via the block generation processing unit (240) (S540). At this time, the header of the block may include connection link information related to connection links accessible to each of the plurality of video segments and interval information generated based on the timestamp information of the start and end times of each of the plurality of video segments.

Furthermore, the medical video management server (200) can perform block updates based on tag information related to the plurality of video segments via the block update processing unit (250) (S550). For example, the corresponding block can be updated based on additional tag information corresponding to each video segment, viewing history, transaction history, usage history, etc.

Furthermore, the medical video management server (200) can track accessor information, access IP information, and access time information as log records (S560). By tracking such access-related information through the corresponding link, access information can be monitored. Also, based on such access-related information, the corresponding block can be updated to prevent tampering with access records.

FIG. 6 is a conceptual diagram illustrating the configuration of a surgical video transmission system using a cache server according to an embodiment of the present invention.

Referring to FIG. 6, the user terminal (400) is a device used by a user such as a doctor or medical staff performing surgery, treatment, consultation, etc., configured to be connectable to, for example, the content server (600), cache server (700), and video segment management server (800), etc. Specifically, it can be any one of, but is not limited to, a smartphone, tablet computer, desktop computer, laptop computer, notebook, workstation, Personal Digital Assistants (PDA), portable computer, wireless phone, mobile phone, e-book, portable multimedia player (PMP), portable game console, digital camera, television, wearable device, Head-Mounted Display (HMD), or Artificial Intelligence (AI) speaker. Furthermore, the user terminal (400) may include a display unit for providing a medical video screen or be configured to be controllable while connected to a display unit.

The user terminal (400) is configured to communicate with various servers, such as the content server (600), cache server (700), and video segment management server (800), via a network (500). The network (500) is a component for performing wired/wireless communication for data transmission/reception between the user terminal (400) and the plurality of servers (600, 700, 800). If the network is a wireless communication network, it may include cellular communication or short-range communication. For example, cellular communication may include at least one of Long-Term Evolution (LTE), LTE Advanced (LTE-A), 5th Generation (5G), Code Division Multiple Access (CDMA), Wideband CDMA (WCDMA), Universal Mobile Telecommunications System (UMTS), Wireless Broadband (WiBro), or Global System for Mobile Communications (GSM). Short-range communication may include at least one of Wi-Fi (Wireless Fidelity), Bluetooth, Zigbee, Near Field Communication (NFC), or Radio Frequency Identification (RFID). However, the communication method is not limited thereto and will include future developed wireless communication technologies.

Next, the content server (600) may be configured to store a plurality of surgical videos. For example, it may be configured to store videos related to surgery, treatment, consultation, etc., recorded in spaces such as operating rooms, treatment rooms, or consultation rooms within a hospital using various types of cameras via the medical video capturing unit (100).

The cache server (700) may be configured to receive and store at least a portion of the surgical video related to the corresponding surgery among the plurality of surgical videos stored in the content server (600), and upon receiving a request for a reference video from the user terminal (400), transmit at least a portion of the surgical video to the user terminal (400). Furthermore, the cache server (700) may be selected as the most advantageous cache server from a plurality of cache servers based on proximity to the location of the corresponding user terminal (400) or response speed.

The video segment management server (800) may be configured to receive surgery-related information including surgery date/time and surgery type, determine the surgical video related to the corresponding surgery among the plurality of surgical videos stored in the content server (600) based on the surgery-related information, and divide the related surgical video into a plurality of video segments each below a predetermined capacity.

These divided video segments are sequentially generated based on the timestamp information of each interval within the corresponding surgical video, and the video segment management server (800) may be configured to transfer at least one video segment corresponding to the beginning part of the plurality of video segments to the cache server (700).

Furthermore, the video segment management server (800) may be configured to transfer at least one video segment to the cache server (700) before the surgery date/time based on the predetermined surgery date/time. For example, based on a predetermined criterion, it can be set to transfer the corresponding video segment to the cache server (700) one day or one hour before the corresponding surgery date/time so that it is stored in the cache server (700) in advance.

Furthermore, the video segment management server (800) may be configured to determine the related surgical video among the plurality of surgical videos stored in the content server (600) based on a similarity judgment with reference video information previously used by the user terminal (400). That is, using the past history data that the user of the user terminal (400) previously referenced or searched, it can determine the surgical video that is highly likely to be referenced during the corresponding surgery.

Furthermore, if at least a predetermined ratio of at least one video segment is streamed by the user terminal (400), it is determined that the user is referencing the corresponding video segment. The cache server (700) may be configured to request, receive, and store the remaining video segments, excluding the beginning part, from the video segment management server (800). By storing the remaining video segments in the cache server (700) in advance, transmission delay can be minimized when streaming the corresponding surgical video through the user terminal (400).

Furthermore, if all of the plurality of video segments are streamed by the user terminal (400), the cache server (700) may be configured to transmit at least a part of a second surgical video, which is next in sequence after the transmitted surgical video, to the user terminal (400). Furthermore, if at least a predetermined ratio of at least one video segment or the entire video segments of the second surgical video is streamed by the user terminal (400), it is determined that the user is referencing the corresponding video segment of the second surgical video. The cache server (700) may be configured to request, receive, and store the remaining video segments, excluding the aforementioned beginning part, from the video segment management server (800).

Furthermore, the video segment management server (800) may be configured to determine at least one key video segment among the plurality of video segments based on at least one of the movement of surgical instruments, the amount of bleeding, and the degree of change in the relevant organ related to the surgery through video analysis of the plurality of video segments using artificial intelligence technology, etc., and transfer the key video segments among the plurality of video segments to the cache server (700). In this way, the video segment management server (800) determines the key video segments considered important among the plurality of video segments and transfers only these key video segments to the cache server (700), thereby efficiently utilizing the limited storage space of the cache server (700).

FIG. 7 is a block diagram illustrating the configuration of a video segment management server according to an embodiment of the present invention. (Note: The original text refers to a cache server in the description for FIG. 7, but the components listed match the Video Segment Management Server 800. The translation assumes this is the intended subject based on FIG. 6 and the component functions described.)

Referring to FIG. 7, the video segment management server (800) according to the present invention may include a surgery information receiving unit (810), a surgical video determination unit (820), a video segmentation processing unit (830), and a video transmission processing unit (840), etc. These components may include programs or program modules executable by one or more processors. The programs or program modules included in the video segment management server (800) may be configured in the form of an operating system, application program, or program, etc., and can be physically stored on various widely used types of storage devices. Such programs or program modules may include various forms such as one or more routines, subroutines, programs, objects, components, instructions, data structures, and for performing specific tasks or executing specific data types, but are not limited thereto.

First, the surgery information receiving unit (810) may be configured to receive surgery-related information including information related to surgery date/time, surgery subject, surgery location, and surgery type, etc., from the user terminal (400) or other servers or terminals managing surgery information.

The surgical video determination unit (820) is configured to determine the surgical video to be provided as a reference video to the user terminal (400). It may be configured to determine the related surgical video among the plurality of surgical videos stored in the content server (600) based on the received surgery-related information. Furthermore, the surgical video determination unit (820) can determine the related surgical video among the plurality of surgical videos stored in the content server (600) based on a similarity judgment with reference video information previously used by the user of the user terminal (400) in relation to the corresponding surgery type, using the previous history information of the user terminal (400).

Furthermore, the surgical video determination unit (820) may be configured to determine at least one key video segment among the plurality of video segments based on at least one of the movement of surgical instruments, the amount of bleeding, and the degree of change in the relevant organ related to the surgery, using video analysis of the plurality of video segments through artificial intelligence technology or operator processing, and transfer only the key video segments among the plurality of video segments to the cache server (700). In this way, by determining the key video segments considered important among the plurality of video segments and transferring only these key video segments to the cache server (700), the limited storage space of the cache server (700) can be efficiently utilized, and medical staff can efficiently utilize their limited time by referencing only the key video segments.

The video segmentation processing unit (830) may be configured to divide the related surgical video determined by the surgical video determination unit (820) into a plurality of video segments each below a predetermined capacity. At this time, the plurality of video segments are sequentially generated based on the timestamp information of each interval within the surgical video, and the video segment management server (800) may be configured to transfer at least one video segment corresponding to the beginning part among the sequentially generated plurality of video segments to the cache server (700) via the video transmission processing unit (840).

The video transmission processing unit (840) is configured to perform transmission processing and transmission schedule management for videos to be transferred to the cache server (700). It can determine one cache server connected to the user terminal (400) based on the proximity to the location of the user terminal (400) or the response speed of each cache server. Furthermore, the video transmission processing unit (840) may be configured to transfer at least one video segment to the cache server (700) before the surgery date/time based on the surgery date/time information included in the surgery-related information.

FIG. 8 is an exemplary diagram illustrating a method for providing a plurality of video segments related to a surgical video using a cache server according to an embodiment of the present invention.

For example, a scheduled surgery may include two types of procedures, and there may be a plan to sequentially proceed with a first surgical video related to a first surgery and a second surgical video related to a second surgery.

First, the first surgical video determined as a reference video related to the first surgery may consist of 5 video segments sequentially generated based on the timestamp information of each interval (t1~t6). The first video segment and the second video segment corresponding to the beginning part may be pre-stored in the cache server. At this time, if the first video segment is fully streamed and viewing is completed beyond the time point t2 via the user terminal (400), the cache server (700) may be configured to request, receive, and store subsequent video segments, e.g., the third, fourth, and fifth video segments, from the video segment management server (800). By transferring and storing subsequent video segments in the cache server (700) in advance based on whether the divided video segments have been viewed, it is possible to ensure that the surgical video targeted for viewing by the user can be watched without delay.

Meanwhile, if video streaming terminates via the user terminal (400) before the predetermined criterion time point t2, it may be determined that the corresponding reference video is unnecessary, and the cache server (700) may be configured not to request subsequent video segments, e.g., video segments after the third video segment. Furthermore, to efficiently manage storage capacity in the cache server (700), if video streaming terminates before a certain time point, the corresponding video segments may be determined as not being of interest to the user and configured to be deleted entirely.

Furthermore, if streaming viewing of the first surgical video is fully completed via the user terminal (400), the cache server (700) may be configured to transmit at least a part of the second surgical video, which corresponds to the next turn, specifically the beginning video segment(s), to the user terminal (400). At this time, if the beginning video segment(s) of the second surgical video are not stored in the cache server (700), the cache server (700) may be configured to request, receive, and pre-store the beginning video segment(s) of the second surgical video from the video segment management server (800), for example, at time point t4 or t5 before the viewing of the first surgical video ends.

FIG. 9 is a flowchart illustrating a surgical video transmission method using a cache server according to an embodiment of the present invention.

First, a plurality of surgical videos can be stored in the content server (600) (S910). At this time, the surgical video may include information such as the type of surgery, surgical subject, interval-specific timestamp information, and tag information.

The video segment management server (800) can receive surgery-related information including surgery date/time and surgery type via the surgery information receiving unit (810) (S920).

The video segment management server (800) can determine the related surgical video based on the surgery-related information via the surgical video determination unit (820) (S930).

The video segment management server (800) can divide the surgical video into a plurality of video segments via the video segmentation processing unit (830) (S940). For example, the surgical video may consist of a plurality of video segments sequentially generated based on the timestamp information of each interval.

The video segment management server (800) can determine one cache server connected to the user terminal (400) based on the proximity to the location of the user terminal (400) or the response speed of each cache server via the video transmission processing unit (840) (S950).

The determined cache server (700) can receive and store some video segments of the related surgical video from the video segment management server (800) (S960).

Upon a request for a surgical reference video from the user terminal (400), some video segments can be provided via streaming through the determined cache server (700) (S970).

Furthermore, the remaining video segments following the initial segments can be requested from the user terminal (400) and provided via streaming through the cache server (700) (S980). If the beginning plurality of segments of the corresponding surgical video are streamed via the user terminal (400) beyond a specific ratio, the cache server (700) can request, receive, and store the subsequent remaining video segments from the video segment management server (800), allowing the entire video to be watched without delay.

FIG. 10 is a conceptual diagram illustrating the configuration of a surgical step video transmission system using a cache server according to an embodiment of the present invention.

The surgical step video transmission system of FIG. 10 has a configuration where a surgical step determination server (900) is added to the configuration of the surgical video transmission system using a cache server shown in FIG. 6.

Here, the content server (600) may be configured to store a plurality of surgical videos.

The video segment management server (800) may be further configured to receive surgery-related information including a surgery type, and based on the received surgery-related information, divide and store the plurality of surgical videos stored in the content server (600) based on detailed surgical steps.

The surgical step determination server (900) may be configured to determine detailed surgical steps based on the surgery type of a surgical patient and determine respective video segments related to each detailed surgical step.

Furthermore, the surgical step determination server (900) may be configured to determine the detailed surgical steps based on record information of a plurality of previous surgical patients who underwent the same type of surgery as the surgical patient. Also, the record information of the previous surgical patients may include at least one of gender, age, surgery timing, underlying diseases, history of other surgeries, post-operative prognosis, and surgical recovery period. That is, when determining the detailed surgical steps, the record information of previous surgical patients can be used to utilize surgical steps and conditions that had good prognosis and recovery periods under conditions similar to the current patient.

Furthermore, the surgical step determination server (900) may be configured to determine the detailed surgical steps by combining the detailed surgical steps of a plurality of previous surgical patients. For example, it may be configured to determine the detailed surgical steps for the current surgical patient by combining the detailed surgical steps of a first previous surgical patient who underwent the same type of surgery as the current surgical patient and the different detailed surgical steps of a second previous surgical patient who underwent the same type of surgery as the current surgical patient.

Furthermore, the surgical step determination server (900) can derive detailed surgical steps that yield the best prognosis and recovery period under conditions similar to the current patient by utilizing the record information of previous patients using a learning model based on artificial intelligence. Accordingly, it may be configured to recommend the optimal detailed surgical steps for the current surgical patient through the AI learning model.

The cache server (700) may be configured to receive and store each of the plurality of video segments related to each detailed surgical step from the video segment management server (800), and upon receiving a request for a detailed surgical step video from the user terminal (400), transmit the plurality of video segments related to the detailed surgical steps determined by the surgical step determination server (900) to the user terminal (400). At this time, the cache server (700) may be determined as the cache server at the optimal location from a plurality of cache servers based on proximity to the location of the user terminal (400) or response speed.

Furthermore, the cache server (700) may be configured to check whether the respective video segments related to each detailed surgical step determined by the surgical step determination server (900) are stored, and for video segments not stored in the cache server (700), receive and store the corresponding video segments from the video segment management server (800) based on the surgical schedule of the surgical patient. For example, the cache server (700) can check the storage status of the respective video segments related to each detailed surgical step before the surgery date/time of the corresponding surgical patient, e.g., 1 hour or one day before, and if unstored video segments exist, request them from the video segment management server (800) to pre-store the corresponding video segments before the surgery date/time.

The user terminal (400) may be configured to receive a plurality of video segments based on the detailed surgical steps determined by the surgical step determination server (900).

FIG. 11 is an exemplary diagram illustrating a configuration for recommending detailed surgical steps for a surgical patient according to an embodiment of the present invention.

A single surgery can be divided into several detailed surgical steps, and video segments can be divided for each detailed surgical step. In FIG. 11, it is assumed that Patient 1, Patient 2, and Patient 3 have records of undergoing the same type of surgery previously, and Patient 4 is scheduled to undergo the same type of surgery.

For example, looking at the previous surgical record of Patient 1, the detailed surgical steps consist of 3 stages: A, B, and C. The previous surgical record of Patient 2 has stage D added between stages A and B, totaling 4 detailed surgical steps. Also, in the previous surgical record of Patient 3, stage E is added after stages A, B, and C, totaling 4 detailed surgical steps. Thus, even for the same type of surgery, some detailed surgical steps may be added or changed depending on the patient's condition and the surgical situation. As such surgical data accumulates, probabilistic judgment regarding the outcomes of detailed surgical steps becomes possible.

For Patient 4, who is scheduled for the same type of surgery as Patients 1 to 3, the detailed surgical steps determined by the surgical step determination server (900) may be a combination of the detailed surgical steps of Patients 1 to 3, comprising a total of 5 detailed surgical steps: A, D, B, C, and E. The detailed surgical step videos corresponding to these 5 steps can be provided as reference videos to the medical staff. Such recommendation proposal and determination of detailed surgical steps can be derived, for example, by using a learning model based on artificial intelligence that utilizes the record information of previous patients to find the detailed surgical steps yielding the best prognosis and recovery period under conditions similar to the current patient. It can find and recommend the detailed surgical step conditions that yield the best prognosis and recovery conditions under similar patient environmental conditions such as same gender, similar age, similar underlying diseases, etc.

FIG. 12 is an exemplary diagram illustrating a method for providing videos of detailed surgical steps using a cache server according to an embodiment of the present invention.

Referring to FIG. 12, the detailed surgical steps for Patient 4 determined by the surgical step determination server (900) may include the A, B, and C stage videos from Patient 1's surgical video, and also include the D stage video from Patient 2's surgical video.

At this time, the cache server (700) can first check the storage status of Patient 1'*s* surgical video and the D stage video from Patient 2's surgical video before the surgery date/time of the corresponding surgical patient. For example, as shown in FIG. 12, if it is determined that all A, B, and C stage videos of Patient 1's surgical video were stored, but the D stage video determined as a detailed surgical step to be referenced from Patient 2's surgical video is not stored, the cache server (700) can request the transmission of the D stage video from Patient 2's surgical video from the video segment management server (800). At this time, the video transmission time can be scheduled so that the cache server (700) receives and stores Patient 2's D stage video before the surgery date/time based on Patient 4's surgical schedule.

While the various methods and systems according to the embodiments of the present invention have been described above in specific diverse embodiments, these are merely examples, and the present invention is not limited thereto and should be interpreted as having the broadest scope according to the basic idea disclosed herein. Those skilled in the art can implement patterns of unstated shapes by combining and substituting the disclosed embodiments, but these also do not depart from the scope of the present invention. In addition, those skilled in the art can easily change or modify the disclosed embodiments based on the present specification, and it is clear that such changes or modifications also fall within the scope of rights of the present invention.

The invention claimed is:

1. A surgical step video transmission system, comprising:

a content server configured to store a plurality of surgical videos;

a video segment management server configured to receive surgery-related information including a surgery type, and based on the surgery-related information, divide and store the plurality of surgical videos stored in the content server based on detailed surgical steps;

a surgical step determination server configured to determine detailed surgical steps based on a surgery type of a surgical patient and determine respective video segments related to each detailed surgical step;

a user terminal configured to receive a plurality of video segments based on the detailed surgical steps determined by the surgical step determination server; and a cache server configured to receive and store respective video segments related to each detailed surgical step from the video segment management server, and upon receiving a request for a detailed surgical step video from the user terminal, transmit the plurality of video segments related to the detailed surgical steps to the user terminal, wherein the cache server is determined from a plurality of cache servers based on proximity to a location or response speed of the user terminal, wherein the cache server is configured to check whether the respective video segments related to each detailed surgical step determined by the surgical step determination server are stored, and for video segments not stored in the cache server, receive and store only a beginning part comprising at least one video segment of the corresponding video segments from the video segment management server before a surgery date/time of the surgical patient based on a surgical schedule of the surgical patient, wherein, when the at least one video segment corresponding to the beginning part is streamed by the user terminal, the cache server is configured to monitor whether at least a predetermined ratio or a predetermined criterion time point of the at least one video segment is streamed, wherein, when the monitored streaming passes the predetermined ratio or the predetermined criterion time point, the cache server is configured to determine that a user is referencing the corresponding video segment, and request, receive and store remaining subsequent video segments from the video segment management server, and wherein, when the monitored streaming terminates before the predetermined ratio or the predetermined criterion time point, the cache server is configured not to request the remaining subsequent video segments and is configured to delete the beginning part initially stored from the cache server to manage storage capacity.

2. The surgical step video transmission system of claim 1, wherein the surgical step determination server is configured to determine the detailed surgical steps based on record information of a plurality of previous surgical patients who underwent the same type of surgery as the surgical patient.

3. The surgical step video transmission system of claim 2, wherein the record information of the previous surgical patients includes at least one of gender, age, surgery timing, underlying diseases, history of other surgeries, post-operative prognosis, and surgical recovery period.

4. The surgical step video transmission system of claim 2, wherein the surgical step determination server is configured to determine the detailed surgical steps for the surgical patient by combining detailed surgical steps of a first previous surgical patient who underwent the same type of surgery as the surgical patient and detailed surgical steps of a second previous surgical patient who underwent the same type of surgery as the surgical patient.

5. The surgical step video transmission system of claim 4, wherein the surgical step determination server is configured to recommend the detailed surgical steps for the surgical patient through a learning model using artificial intelligence.

6. A surgical step video transmission method, comprising:

storing a plurality of surgical videos in a content server;

receiving, at a video segment management server, surgery-related information including a surgery type, and based on the surgery-related information, dividing and storing the plurality of surgical videos stored in the content server based on detailed surgical steps;

determining, at a surgical step determination server, detailed surgical steps based on a surgery type of a surgical patient and determining respective video segments related to each detailed surgical step;

receiving, at a user terminal, a plurality of video segments based on the detailed surgical steps determined by the surgical step determination server;

determining a cache server from a plurality of cache servers based on proximity to a location or response speed of the user terminal or response speed;

receiving and storing, at the determined cache server, respective video segments related to each detailed surgical step from the video segment management server;

transmitting, from the determined cache server to the user terminal, the plurality of video segments related to the detailed surgical steps upon receiving a request for a detailed surgical step video from the user terminal;

checking, at the determined cache server, whether the respective video segments related to each detailed surgical step determined by the surgical step determination server are stored;

for video segments not stored in the determined cache server, receiving and storing, at the determined cache server, only a beginning part comprising at least one video segment of the corresponding video segments from the video segment management server before a surgery date/time of the surgical patient based on a surgical schedule of the surgical patient;

when the at least one video segment corresponding to the beginning part is streamed by the user terminal, monitoring, at the determined cache server, whether at least a predetermined ratio or a predetermined criterion time point of the at least one video segment is streamed;

when the monitored streaming passes the predetermined ratio or the predetermined criterion time point, determining, by the determined cache server, that a user is referencing the corresponding video segment, and requesting, receiving and storing remaining subsequent video segments from the video segment management server; and when the monitored streaming terminates before the predetermined ratio or the predetermined criterion time point, not requesting, by the cache server, the remaining subsequent video segments, and deleting the beginning part initially stored from the cache server to manage storage capacity.

* * * * *